United States Patent
Lisk, Jr. et al.

(10) Patent No.: US 7,160,264 B2
(45) Date of Patent: Jan. 9, 2007

(54) ARTICLE AND METHOD FOR OCULAR AQUEOUS DRAINAGE

(75) Inventors: James R. Lisk, Jr., Suwanee, GA (US); James E. Memmen, Green Bay, WI (US); Scott M. Hampton, Cumming, GA (US); Robert E. Nordquist, Oklahoma, OK (US); Philip Vincent Robledo, Duluth, GA (US); Ming-Kok Tai, Lawrenceville, GA (US)

(73) Assignee: Medtronic-Xomed, Inc., Jacksonville, FL (US)

( * ) Notice: Subject to any disclaimer, the term of this patent is extended or adjusted under 35 U.S.C. 154(b) by 200 days.

(21) Appl. No.: 10/737,707

(22) Filed: Dec. 16, 2003
(Under 37 CFR 1.47)

(65) Prior Publication Data

US 2004/0260227 A1    Dec. 23, 2004

Related U.S. Application Data

(60) Provisional application No. 60/434,946, filed on Dec. 19, 2002.

(51) Int. Cl.
*A61M 5/00* (2006.01)
*A61M 35/00* (2006.01)
(52) U.S. Cl. .......................................... 604/8; 604/294
(58) Field of Classification Search .............. 604/7–10, 604/264; 623/4.1, 5.11, 6.16, 6.11; 606/107–108, 606/109, 167, 170
See application file for complete search history.

(56) References Cited

U.S. PATENT DOCUMENTS

| | | | |
|---|---|---|---|
| 4,037,604 A | 7/1977 | Newkirk | |
| 4,402,681 A | 9/1983 | Haas et al. | |
| 4,428,746 A | 1/1984 | Mendez | |
| 4,521,210 A | 6/1985 | Wong | |
| 4,722,724 A | 2/1988 | Schocket | |
| 4,750,901 A | 6/1988 | Molteno | |
| 4,787,885 A | 11/1988 | Binder | |
| 4,826,478 A | 5/1989 | Schocket | |

(Continued)

FOREIGN PATENT DOCUMENTS

AT    409 586 B    9/2002

(Continued)

OTHER PUBLICATIONS

'Ex-PRESS Miniature Glaucoma Implant,' Optonol-Product Information, http://www.optonal.com/info.html, (date unknown), pp. 1-6.

*Primary Examiner*—Tatyana Zalukaeva
*Assistant Examiner*—Leslie R. Deak
(74) *Attorney, Agent, or Firm*—Dicke, Billig & Czaja, PLLC

(57) ABSTRACT

An ophthalmic implant having a body for positioning in a recess created in the sclera, feet for positioning in the anterior chamber, and a neck between the body and the feet for positioning in a scleral opening created between the scleral recess and the anterior chamber. The implant feet extend beyond the implant body and have a curvature approximating the curvature of the anterior chamber. The implant has drainage passageways for draining ocular fluid from the anterior chamber. The passageways are formed in outer surfaces or through the interior of the implant. Interior passageways are formed in surfaces of layers of the implant or by voids in inner layers of the implant. Related methods include creating undercuts that receive outer portions of the implant body and creating a scleral opening that is longer than the implant neck.

20 Claims, 4 Drawing Sheets

U.S. PATENT DOCUMENTS

| | | | |
|---|---|---|---|
| 4,936,825 A * | 6/1990 | Ungerleider | 604/8 |
| 4,946,436 A | 8/1990 | Smith | |
| 5,041,081 A | 8/1991 | Odrich | |
| 5,092,837 A | 3/1992 | Ritch et al. | |
| 5,342,370 A | 8/1994 | Simon et al. | |
| 5,372,577 A | 12/1994 | Ungerleider | |
| 5,397,300 A | 3/1995 | Baerveldt et al. | |
| 5,433,701 A * | 7/1995 | Rubinstein | 604/8 |
| 5,454,796 A | 10/1995 | Krupin | |
| 5,476,445 A | 12/1995 | Baerveldt et al. | |
| 5,520,631 A | 5/1996 | Nordquist et al. | |
| 5,558,630 A | 9/1996 | Fisher | |
| RE35,390 E | 12/1996 | Smith | |
| 5,626,558 A | 5/1997 | Suson | |
| 5,626,559 A | 5/1997 | Solomon | |
| 5,651,782 A | 7/1997 | Simon et al. | |
| 5,681,275 A | 10/1997 | Ahmed | |
| 5,702,414 A | 12/1997 | Richter et al. | |
| 5,704,907 A | 1/1998 | Nordquist et al. | |
| 5,713,844 A | 2/1998 | Peyman | |
| 5,743,868 A | 4/1998 | Brown et al. | |
| 5,882,327 A | 3/1999 | Jacob | |
| 5,893,837 A | 4/1999 | Eagles et al. | |
| 5,968,058 A | 10/1999 | Richter et al. | |
| 6,001,128 A | 12/1999 | Graff et al. | |
| 6,050,970 A | 4/2000 | Baerveldt | |
| 6,102,045 A | 8/2000 | Nordquist et al. | |
| 6,186,974 B1 | 2/2001 | Allan et al. | |
| 6,203,513 B1 | 3/2001 | Yaron et al. | |
| 6,383,218 B1 | 5/2002 | Sourdille et al. | |
| 6,383,219 B1 | 5/2002 | Telandro et al. | |
| 6,450,984 B1 | 9/2002 | Lynch et al. | |
| 6,736,791 B1 * | 5/2004 | Tu et al. | 604/8 |
| 2004/0092856 A1 * | 5/2004 | Dahan | 604/8 |
| 2004/0098123 A1 * | 5/2004 | Freeman et al. | 623/4.1 |

FOREIGN PATENT DOCUMENTS

| | | |
|---|---|---|
| DE | 19947711 A1 | 5/2001 |
| EP | 0 214 853 B1 | 11/1994 |
| NL | C 1005694 | 4/1997 |
| PL | 9203341-5 A | 3/1994 |
| SU | 1316114 A1 | 3/1988 |
| SU | 1535542 A1 | 1/1990 |
| SU | 1797884 A1 | 2/1993 |
| SU | 1805938 A3 | 3/1993 |
| WO | WO 94/13234 | 6/1994 |
| WO | WO 95/35078 | 12/1995 |
| WO | WO 01/79656 A2 | 10/2001 |
| WO | WO 02/17832 A1 | 3/2002 |
| WO | WO 02/32343 A2 | 4/2002 |
| WO | WO 02/080811 A2 | 10/2002 |

* cited by examiner

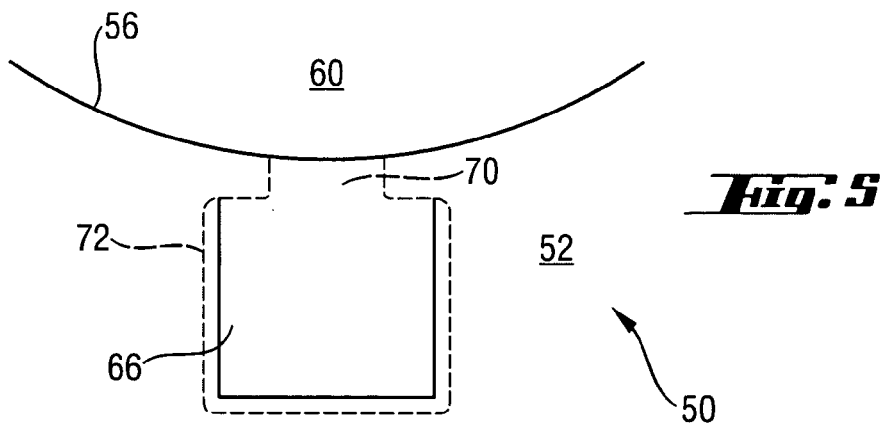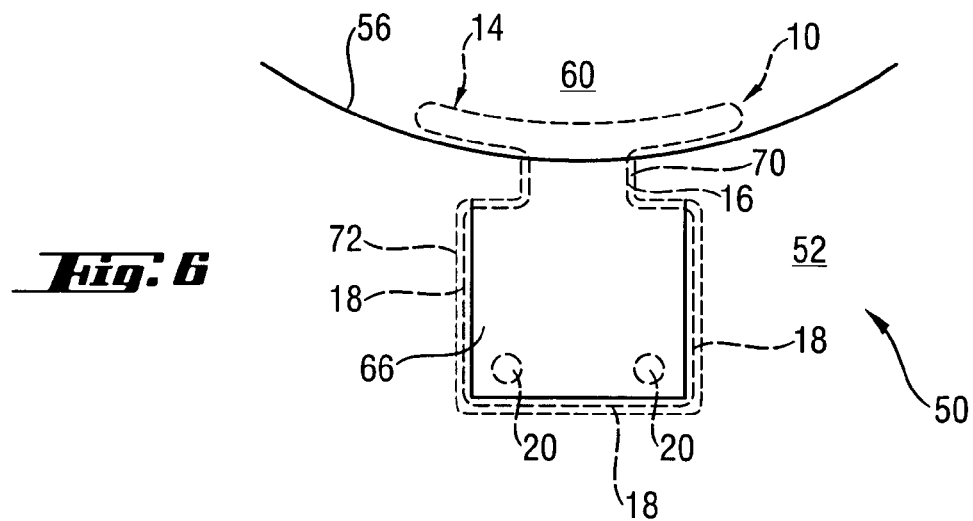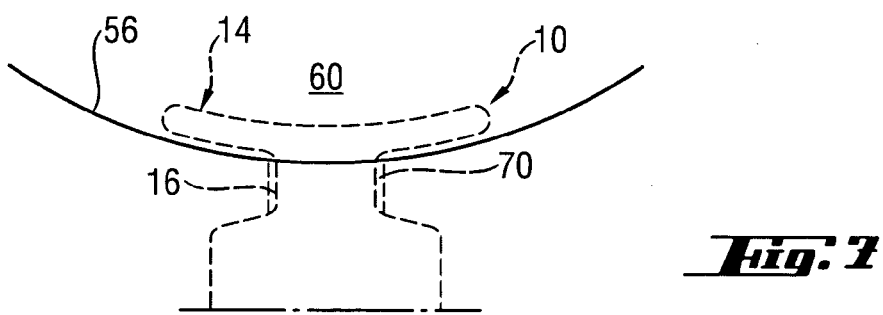

ARTICLE AND METHOD FOR OCULAR AQUEOUS DRAINAGE

CROSS-REFERENCE TO RELATED APPLICATION

This application claims the benefit of U.S. Provisional Patent Application Ser. No. 60/434,946, filed Dec. 19, 2002, the entirety of which is hereby incorporated herein by reference for all purposes.

TECHNICAL FIELD

This invention relates generally to ophthalmic implants and surgical techniques for lowering the intraocular pressure of an eye and, more particularly, for draining ocular aqueous fluid from the anterior chamber of the eye in the treatment of glaucoma.

BACKGROUND OF THE INVENTION

Glaucoma is an eye disorder that afflicts many people and, if left untreated, can result impaired vision, and blindness. The disorder is characterized by progress optic neuropathy, often associated with high intraocular pressure (IOP) in the eye. The high IOP is caused by poor outflow of ocular fluid, the aqueous humor, from the anterior chamber behind the cornea. For most persons with glaucoma, the high IOP is caused by insufficient outflow of the aqueous humor from the anterior and posterior chambers of the eye due to the deterioration or blockage of the outflow route.

The focus of most treatments for glaucoma is in reducing the IOP. Conventional treatments for reducing IOP include medications, laser trabeculoplasty surgery, glaucoma filtration surgery and glaucoma shunt implantation surgeries. Many of the medications, including antimetabolites, reduce the formation of aqueous humor and have undesirable side-effects. In some glaucoma surgeries, an ophthalmic implant or shunt is implanted in the eye to facilitate drainage of the aqueous humor from the anterior chamber. Examples of such ophthalmic implants and a background discussion of glaucoma are disclosed by U.S. Pat. No. 5,520,631, U.S. Pat. No. 5,704,907, and U.S. Pat. No. 6,102,045, all granted to Nordquist et al., and all of which are hereby incorporated herein by reference.

These ophthalmic implants have, in some cases, provided an improvement in the drainage of aqueous humor from the anterior chamber, thereby reducing the IOP in the eyes of glaucoma patients and reducing the risk of vision loss. However, it has been observed that sometimes the implants are not as stable in the eye as would be ideal, so that they could migrate from their implanted position, resulting in the loss of efficacy and other complications. In addition, the implants are typically made of a porous material for permitting drainage through them. But the amount of drainage is limited by the fluid transport characteristics of the porous implant material in the cited devices.

Accordingly, a need remains in the art for a way to reduce IOP by implanting an ophthalmic implant that facilitates increased drainage of the aqueous humor fluid from the anterior chamber of the eye. In addition, there is a need for an ophthalmic implant and techniques for implanting it that result in the implant being more stable in the eye. Furthermore, there is a need for such an implant that is time and cost-effective to manufacture and implant. It is to the provision of such methods and articles that the present invention is primarily directed.

SUMMARY OF THE INVENTION

Briefly described, the present invention provides an ophthalmic implant for implanting in the eye of persons or animals with glaucoma to reduce intraocular pressure (IOP). The implant has a body, one or more feet, and a neck between the body and the feet. The body can be positioned under a flap and in a recess surgically created in the sclera, the feet can be positioned in the anterior chamber, and the neck can be positioned in an opening surgically created in the sclera between the scleral recess and the anterior chamber. In this way, the implant can be implanted in the eye to permit ocular fluid, the aqueous humor, to drain out of the anterior chamber.

In a first exemplary embodiment, the implant body has outer portions that can be tucked into undercuts created at bottom corners of and extending outward from the scleral recess. With the outer portions of the body tucked into the undercuts, the implant is held more securely in place in the eye. Also, the body is manufactured with suture holes for receiving sutures to secure the implant to the sclera. This further increases the stability of the implant, and eliminates the need for surgeons to create suture holes during surgical implantation.

The feet preferably have a curvature that is approximately the same as the curvature of the anterior chamber at the sclera, which is near 11 millimeters diameter for adult humans. In this way, the curved feet seat nicely within the anterior chamber to provide increased implant stability. Also, the feet extend beyond the width of the body so that if the sutures fail the feet are still unlikely to migrate from the anterior chamber. This further increases the stability of the implant in the eye.

The neck preferably has a length that is greater than known implants so that during implantation, the scleral recess may be cut a safe distance from the anterior chamber. This reduces the need for precise surgical cuts and reduces the chance that a cut may penetrate into the anterior chamber, which would ruin that site for implantation. Also, the length of the neck may be less than the length of the scleral opening. In this way, the neck is under tension, which tends to increase the stability of the implant in the eye.

In other embodiments, the implant has one or more drainage passageways for the ocular fluid to flow through out of the anterior chamber and into the sclera for dispersing by lymphatic vessels. The drainage passageways are formed in the outer surfaces of the implant, in the interior of the implant, or both. In this way, the drainage passageways facilitate increased ocular fluid flow from the anterior chamber, thereby increasing the aqueous humor outflow rate and reducing the intraocular pressure.

In a second exemplary embodiment, the implant has one or more longitudinal drainage passageways along the length of the implant. In a third exemplary embodiment, the implant has one or more lateral drainage passageways across the width of the implant. In a fourth exemplary embodiment, the implant has one or more surface drainage passageways provided by channels in both outer surfaces of the implant. In a fifth exemplary embodiment, the implant is made of at least two layers and has one or more interior drainage passageways provided by surface channels in inner-facing surfaces of the implant layers. And in a sixth exemplary embodiment, the implant is made of at least three layers and has one or more interior drainage passageways provided by voids in an inner layer of the implant.

In addition, the present invention provides surgical techniques for implanting ophthalmic implants in the eyes of persons or animals with glaucoma to reduce IOP. An exemplary method includes the steps of creating a recess in the sclera, creating an opening in the sclera between the scleral recess and the anterior chamber, creating one or more undercuts in the sclera extending outward from the scleral recess, providing an ophthalmic implant having a body and one or more feet, inserting the feet of the ophthalmic implant through the scleral opening and into the anterior chamber, and inserting the body of the ophthalmic implant into the scleral recess with outer portions of the implant body extending into the scleral undercuts. Preferably, the scleral undercuts are made at the bottom corners of the scleral recess. In this way, the outer portions of the implant body are secured in the scleral undercuts to stabilize the ophthalmic implant in the eye while ocular fluid drains out of the anterior chamber.

Furthermore, the scleral opening is preferably made with a length that is greater than the length of the neck of the implant body. Therefore, the neck is under tension when implanted into the eye to stabilize the implant in the eye.

Accordingly, the present invention provides an improved ophthalmic implant for treating glaucoma patients by lowering the IOP in their eyes. The ophthalmic implant has one or more drainage passageways that promote increased drainage of the aqueous humor fluid from the anterior chamber of the eye. In addition, the invention provides an implant with a uniquely configured body, feet, and neck to increase the stability of the implant in the eye. Furthermore, the present invention provides methods for implanting an implant in the eye of a glaucoma patient to better stabilize the implant in the patient's eye.

BRIEF DESCRIPTION OF THE DRAWING FIGURES

FIG. 5 is a plan view of the eye portion of FIG. 3, after the undercuts have been made in the sclera.

FIG. 6 is a plan view of the eye portion of FIG. 3, after the implant has been surgically implanted in the eye.

FIG. 7 is a plan view of the eye portion of FIG. 3, showing the scleral opening made with a length that is greater than the length of the implant neck, according to another exemplary implantation method.

DETAILED DESCRIPTION OF THE EXEMPLARY EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of "about," "approximately," or the like, it will be understood that the particular value forms another embodiment.

The present invention provides ophthalmic implants and surgical methods for implanting them in the eyes of people or animals suffering from glaucoma to reduce intraocular pressure (IOP). When using these implants and methods, outflow of ocular fluid, the aqueous humor, from the anterior chamber of the patient's eyes is increased while better stabilizing the implant in the eye. This eliminates or at least significantly reduces the likelihood of glaucoma resulting in blindness.

Figure 1:
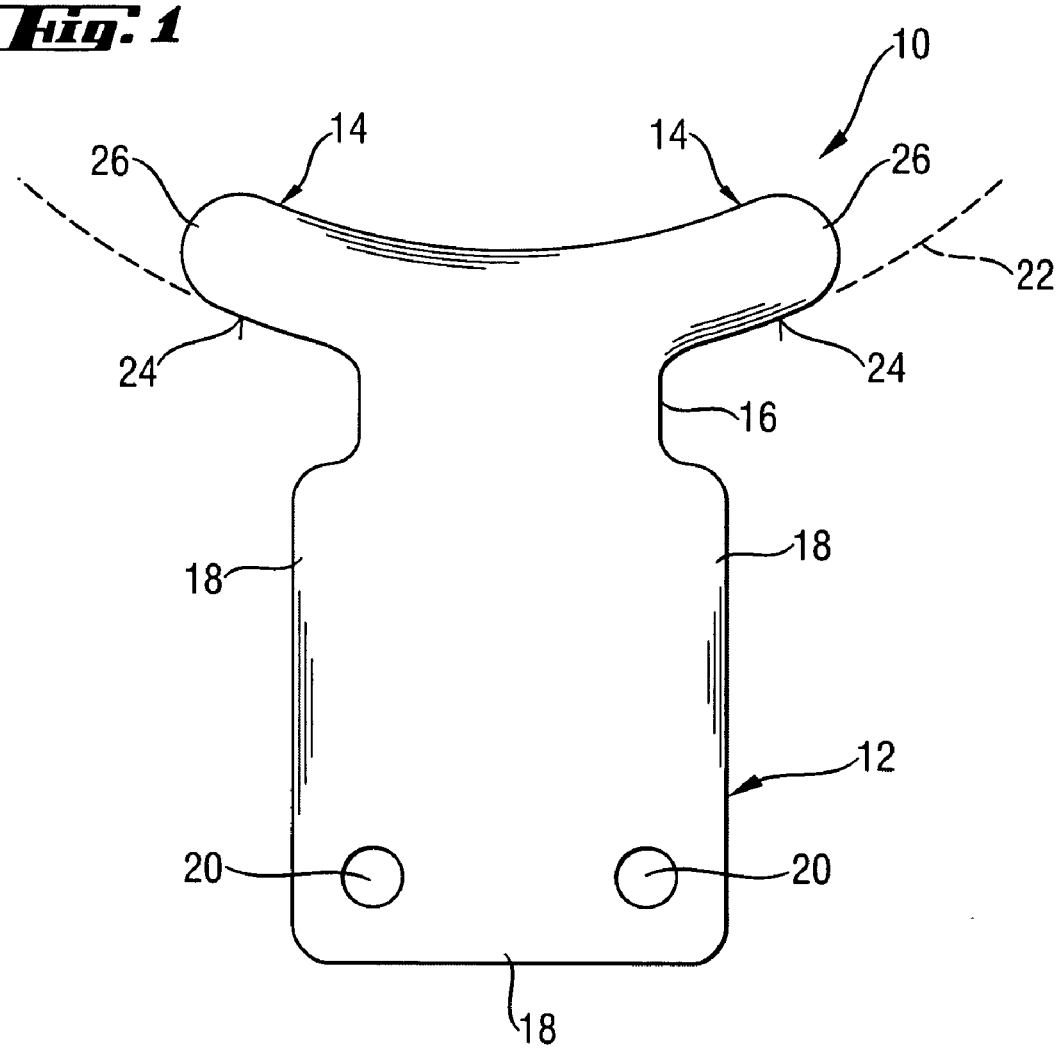
FIG. 1 is a plan view of an ophthalmic implant according to a first exemplary embodiment of the present invention, showing the implant having a body, feet, and a neck between the body and the feet.
Figure 2:
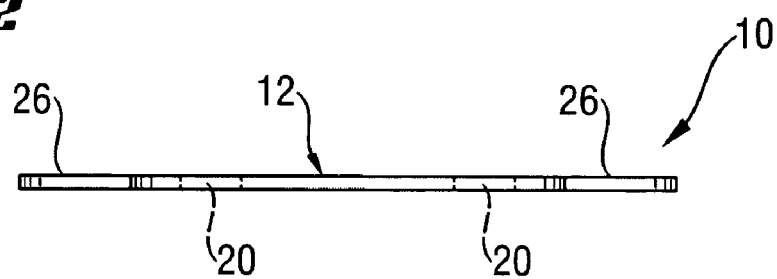
FIG. 2 is a side view of the implant of FIG. 1.

Referring now to the drawing figures, wherein like reference numerals represent like parts throughout the several views, FIGS. 1 and 2 show an ophthalmic implant according to a first exemplary embodiment of the present invention, generally referred to as the implant 10. The implant 10 has a body 12, one or more feet 14, and a neck 16 between the body and the feet. The body 12 can be positioned under a flap and in a recess surgically created in the sclera, the feet 14 can be positioned in the anterior chamber, and the neck 16 can be positioned in an opening surgically created in the sclera between the scleral recess and the anterior chamber.

Preferably, the implant body 12 is generally rectangular. Alternatively, the body 12 can be triangular, polygonal, or it can have another shape. In a typical commercial embodiment, the body 12 is about 4.0 mm long and about 3.5 mm wide.

The implant body 12 has outer portions 18 that can be tucked into undercuts created at bottom corners of and extending outward from the scleral recess. With the outer portions 18 of the body 12 tucked into the undercuts, the implant 10 is held more securely in place in the eye. In a typical commercial embodiment, the body 12 has about 0.1 to 0.05 mm outer portions 18 at three sides. Alternatively, the body can have the outer portions 18 at only one or two sides. The outer portions 18 are typically the same thickness as the rest of the body 12.

In addition, the implant body 12 is manufactured with suture holes 20 for receiving sutures to secure the implant to the sclera. Conventional implants typically do not have suture holes, so the surgeon has to pierce the implant body during the implantation surgery to suture the implant in place in the eye. The suture holes 20 in the body 12 simplify the operation by eliminating the need for surgeons to create the suture holes during surgical implantation.

The implant feet 14 have a curvature 22 that is approximately the same as the curvature of the anterior chamber at the sclera of the patient. In a typical commercial embodiment, the curvature 22 has a radius of about 5.5 mm. This junction of the sclera and the anterior chamber (formed by the space under the cornea) is known as the limbus corneae, or the anterior chamber angle, or simply, the angle. Because the feet 22 are so curved, they seat with a close fit against the limbus corneae. While the seating edge 24 of the feet 14 is so curved, the opposite edge need not be curved.

In addition, the feet 14 have outer portions 26 that extend beyond the width of the body 12. In a typical commercial embodiment, the feet 14 extend about 1.5 mm from the neck and the outer portions 26 extend about 1.0 mm beyond the body 12. Because of the outer portions 26, the feet 14 are long enough that they do not work their way out of the anterior chamber through the scleral opening. So if the sutures were to fail, the outer portions 26 of the feet 14 keep the implant 10 securely in place on the eye.

The implant neck 16 has a reduced width, relative to the body 12 and feet 16. Additionally, the implant neck 16 has a greater length than previously cited implants. With the previously cited implants having very short necks provided by a slit or notch, the surgeon must cut the scleral recess close (within a small fraction of a millimeter) to the limbus corneae. If the cut is too deep, it will penetrate into the anterior chamber and the opening may allow the feet 14 to pass through it even when unfolded. Because the feet 14 could then migrate out of the anterior chamber and into the scleral, this site cannot then be used for the conventional implant. And because of the position of the rectus muscle, there are only four scleral sites where the implant can be readily implanted. But the neck 16 of the present implant 10 is sufficiently long that the body 12 is spaced apart from the anterior chamber so that the scleral recess does not need to be created immediately adjacent to the anterior chamber. In a typical commercial embodiment, the neck 16 is about 0.8 mm long, about one-fifth of the length of the body 12.

In addition, the length of the neck 16 is less than the length of the scleral opening created between the scleral recess and the anterior chamber. For example, as just mentioned the neck 16 can be about 0.8 mm long and the scleral opening can be made about 1.0 mm long, which is the approximate thickness of the limbus corneae transition between the sclera and the cornea. So when the implant 10 is positioned in the eye, the neck 16 is under tension. And the part of the sclera between the scleral recess and the anterior chamber is under compression. By placing the neck 16 under tension, the implant is less able to shift and migrate in the eye.

Preferably, the implant 10 is made of regenerated cellulose, though other materials or a combination of materials with the desired strength, softness, flaccidness, and ocular biocompatibility may be selected. Preferably, the material is flexible for conforming the shape of the eye and so the feet can fold in for implanting. The implant 10 can be manufactured by die-cutting or other fabrication techniques. In a typical commercial embodiment, the implant 10 has a generally uniform thickness of about 80 to 250 microns.

Referring now to FIGS. 3–6, the present invention also provides surgical techniques for implanting the ophthalmic implant 10 in the eye of a person or animal with glaucoma to reduce IOP. It will be understood that these exemplary methods can be used with other implants as long as they have the body outer portions 18 and/or the neck 16 of the implant 10 as described above.

Figure 3:
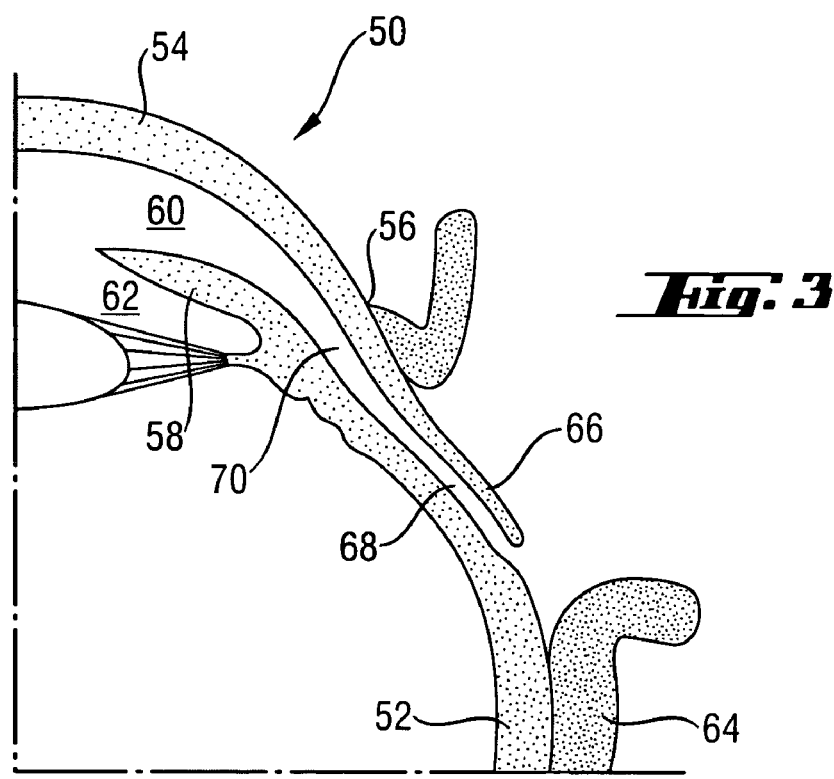
FIG. 3 is a cross-sectional view of a portion of an eye surgically prepared for implanting the ophthalmic implant of FIG. 1 according to an exemplary implantation method, showing a flap and recess created in the sclera of the eye.

FIG. 3 shows a portion of an eye 50 that has been surgically prepared for implanting the ophthalmic implant 10. The eye 50 has a sclera 52, a cornea 54, an angle 56 at the junction of the sclera and the cornea, an iris 58, an anterior chamber 60 between the cornea and the iris, a posterior chamber 62 behind the iris, and a conjunctiva 64 covering the sclera. The surgical preparation includes the steps of creating a flap 66 and thus a recess 68 under the flap in the sclera 52, and creating an opening 70 in the sclera between the scleral recess 66 and the anterior chamber 60. The scleral recess 68 is made with a size and shape for receiving the implant body 12 (but not the outer portions 18 of the body), and the scleral opening 70 is made with a size and shape for passing through it the implant neck 16 and the implant feet 14 when folded in.

Figure 4:
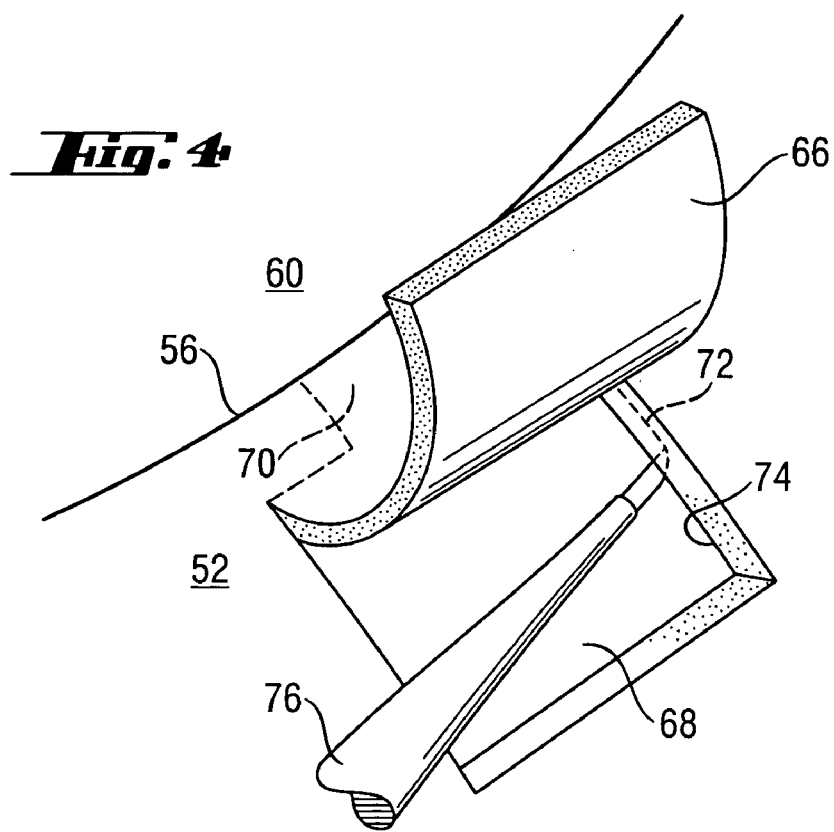
FIG. 4 is a perspective view of the eye portion of FIG. 3, showing undercuts being made at bottom corners of the scleral recess.

As shown in FIGS. 4 and 5, the surgical preparation further includes the step of creating undercuts 72 in the sclera 52 extending outward from the scleral recess 68. The undercuts 72 are made with a size and shape for receiving the outer portions 18 of the implant body 12. For example, the undercuts 72 can be made about 0.1 to 0.5 mm outward from the scleral recess 68 for receiving outer portions 18 of about the same size. The undercuts 72 can be made at three sides of the scleral recess 68, or at fewer or more sides if so desired. Preferably, the undercuts 72 are made at bottom corners 74 of the scleral recess 68. The scleral recess 68, scleral opening 70, and scleral recess undercuts 72 are preferably made by cutting with a scalpel 76, but they could alternatively be made by a laser or by another surgical technique.

FIG. 6 shows the implant 10 inserted into the eye 10. The insertion steps include folding in the implant feet 14 and inserting the folded feet and the neck 16 through the scleral opening 70 so that the feet are inserted into the anterior chamber 60 and the neck is positioned in the scleral opening 70. The elasticity of the implant material causes the feet 14 to unfold so that they do not migrate down out of the anterior chamber. The insertion steps further include inserting the implant body 12 into the scleral recess 68 under the scleral flap 66 and inserting the body outer portions 18 into the undercuts 72. With the implant body 12 nested within the scleral recess 68 and the body outer portions 18 tucked into the scleral undercuts 72, the implant 10 is constrained from shifting around on the eye 50.

After the implant 10 is inserted in the desired position in the eye 50, sutures can be sewn into the sclera 52 through the suture holes 20 in the implant 10 to further stabilize it in place. And the scleral flap 66 is sutured close to promote proper healing and help stabilize the implant 10.

In another exemplary implantation method shown in FIG. 7, the scleral opening 70 is made with a length that is greater than the length of the implant neck 16. To do this, the sceral flap 66 and recess 68 are not made as close to the cornea 54. For example, when using an implant 10 with a 0.8 mm long neck 16, the scleral opening 70 may be made about 1.0 mm long, which is about the thickness of the limbus corneae, so the sceral flap 66 and recess 68 are made up to about 1.0 mm from the cornea 54. This puts the neck 16 under tension when it is implanted into the eye 50, and compresses the portion of the sclera 52 between the scleral recess 68 and the anterior chamber 60. With the implant neck 16 under tension, it is better held in place and stabilized in the eye. It will be understood that this method can be performed in conjunction with the undercutting method described above or separately.

Turning now to FIGS. 8–12, in other exemplary embodiments of the present invention the implant has one or more drainage passageways for the ocular fluid to flow through out of the anterior chamber 60 and into the sclera 52. After implanting the implant, the scleral flap 66 tends to heal back into its original position. After healing, ocular fluid need not flow out of the scleral through the scleral flap incisions because the lymphatic vessels in the sclera 52 absorb and disperse the ocular fluid. In order to increase the amount of ocular fluid drained out of the anterior chamber 60, the implant is provided with the drainage passageways to facilitate ocular fluid drainage to the sclera 52 for dispersing by the lymphatic vessels. The drainage passageways are formed in the outer surfaces of the implant, in the interior of the implant, or in both. The drainage passageways may be formed by die-stamping, laser ablation or by other fabrication techniques.

Figure 8:
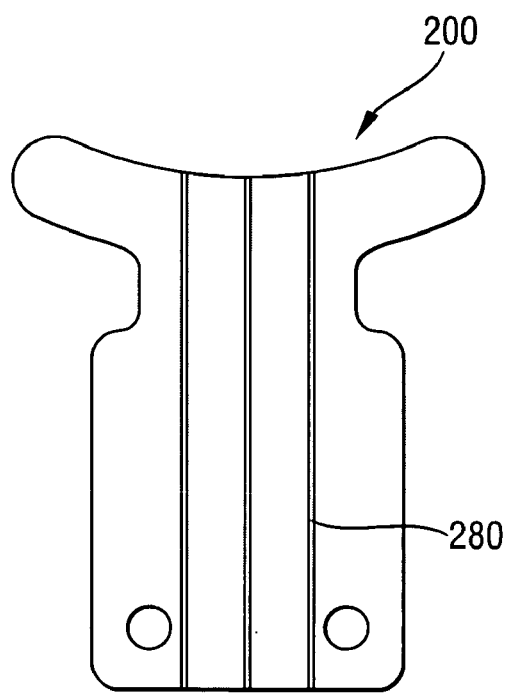
FIG. 8 is a plan view of an ophthalmic implant according to a second exemplary embodiment of the present invention, showing the implant having longitudinal drainage passageways.

FIG. 8 shows a second exemplary embodiment of the invention with the implant 200 having drainage passageways provided by longitudinal drainage passageways 280. The longitudinal drainage passageways 280 provide a route for the ocular fluid to flow through, instead of just migrating through the cellulose material of the implant 200. Any number of the longitudinal drainage passageways 280 can be provided, depending on the amount of drainage desired and limitations imposed by the size of the implant 200.

Figure 9:
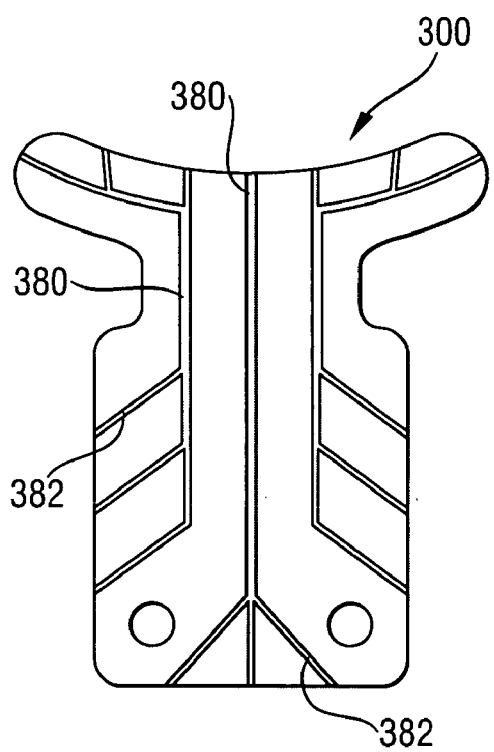
FIG. 9 is a plan view of an ophthalmic implant according to a third exemplary embodiment of the present invention, showing the implant also having lateral drainage passageways.

FIG. 9 shows a third exemplary embodiment of the invention with the implant 300 having drainage passageways provided by longitudinal drainage passageways 380 as well as lateral drainage passageways 382. The lateral drainage passageways 382 deliver the ocular fluid across the implant 300 to its sides for dispersing the fluid over a larger area into the sclera 52 for better absorption by the lymphatic vessels. If desired, main portions of the longitudinal drainage passageways 380 and/or the lateral drainage passageways 382 may be thicker or deeper than branch portions, so as not to create a bottleneck in the fluid flow delivery system. Any number of the lateral drainage passageways 382 may be provided, depending on the amount of drainage desired and limitations imposed by the size of the implant 200. Of course, the implant 300 may be provided with the lateral drainage passageways 382 but without the longitudinal drainage passageways 380, if so desired.

Figure 10:
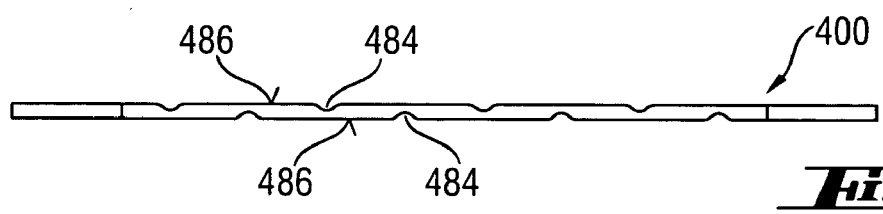
FIG. 10 is a side view of an ophthalmic implant according to a fourth exemplary embodiment of the present invention, showing the implant having drainage passageways formed by channels in both outer surfaces of the implant.

FIG. 10 shows a fourth exemplary embodiment of the invention with the implant 400 having the drainage passageways formed by channels 484 in both outer surfaces 486 of the implant. The channels 484 may be configured in alignment with each other (one over another), or they may be staggered in a regular or irregular pattern.

Figure 11:
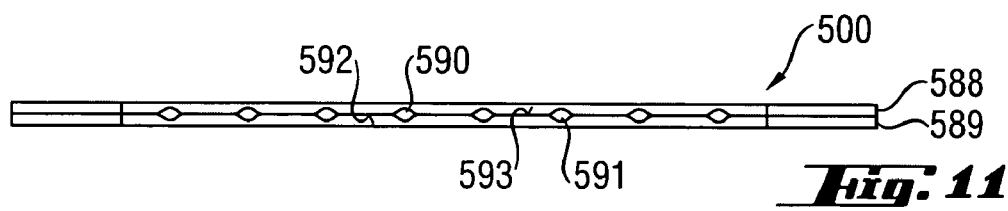
FIG. 11 is a side view of an ophthalmic implant according to a fifth exemplary embodiment of the present invention, showing the implant made of two layers and having drainage passageways formed by channels in inner-facing surfaces of the implant.

FIG. 11 shows a fifth exemplary embodiment of the invention with the implant 500 made of two layers 588 and 589, and having the drainage passageways formed by channels 590 and 591 in inner-facing surfaces 592 and 593 of the implant layers. The layers 588 and 589 may be laminated together or folded over each other, and more than two layers may be provided, if desired. The channels 590 and 591 may be configured to align with each other (one over another), or they may be staggered in a regular or irregular pattern.

Figure 12:
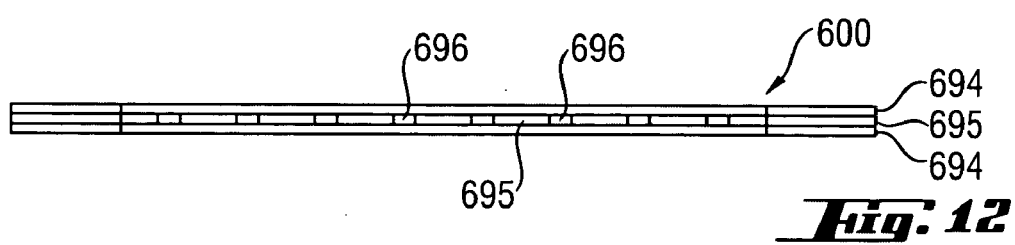
FIG. 12 is a side view of an ophthalmic implant according to a sixth exemplary embodiment of the present invention, showing the implant made of three layers and having drainage passageways formed by voids in the inner layer of the implant.

FIG. 12 shows a sixth exemplary embodiment of the invention with the implant 600 made of three layers, with two outer layers 694 and one inner layer 695. The drainage passageways are formed by one or more voids 696 in the inner layer 695 of the implant 600. The layers 694 and 695 may be laminated together or folded over each other, and more than one inner layer may be provided, if desired. And the layers 694 and 695 may have also surface channels in alignment with the voids 696 or staggered in a regular or irregular pattern.

In another embodiment contemplated by the present invention, the implant feet extend directly from the body instead of indirectly from the body with the neck in between. The body does not migrate through the scleral opening into the anterior chamber, however, because the sutures hold it in place. In still another embodiment, the implant has dimensions that are larger than or smaller than those of the typical commercial embodiments for an average-sized adult as described above. For example, smaller implants could be used for children and/or pets, and larger ones for large adults and/or animals.

Accordingly, the present invention provides an improved ophthalmic implant for lowering the IOP in the eyes of glaucoma patients. In some embodiments, the ophthalmic implant has one or more drainage passageways formed in the outer surfaces and/or the interior of the implants to drain more ocular fluid out of the anterior chamber of the eye. In further embodiments, the implant has a uniquely configured body, feet, and/or neck to increase the stability of the implant in the eye. Furthermore, the present invention provides surgical implantation methods including providing undercuts and scleral openings sized to better stabilize the implants securely in place. And the implants are preferably of a simple construction using known materials such that they are time and cost-effective to manufacture and implant.

While the invention has been disclosed in exemplary forms, those skilled in the art will recognize that many modifications, additions, and deletions can be made therein without departing from the spirit and scope of the invention as set forth in the following claims.

What is claimed is:

1. A method of lowering the intraocular pressure of an eye having a sclera and an anterior chamber, the method comprising:
   a) creating a recess in the sclera;
   b) creating an opening in the sclera between the scleral recess and the anterior chamber;
   c) creating one or more undercuts in the sclera extending outward from the scleral recess;
   d) providing an ophthalmic implant having a body and one or more feet;
   e) inserting the feet of the ophthalmic implant through the scleral opening and into the anterior chamber; and
   f) inserting the body of the ophthalmic implant into the scleral recess with outer portions of the implant body extending into the scleral undercuts, wherein the implant body outer portions in the scleral undercuts help stabilize the ophthalmic implant in the eye while ocular fluid drains out of the anterior chamber.

2. The method of claim 1, wherein the step of creating the scleral undercuts comprises creating one or more undercuts at bottom corners of the scleral recess.

3. The method of claim 1, wherein the ophthalmic implant has a neck between the body and the feet, and the step of creating the scleral opening comprises creating an opening in the sclera between the scleral recess and the anterior chamber with a length that is greater than a length of the neck, wherein the neck is under tension when implanted into the eye to stabilize the implant in the eye.

4. An ophthalmic implant for lowering the intraocular pressure of an eye having a sclera and an anterior chamber, the implant comprising:
   a) a body configured to be positioned in a recess in the sclera;
   b) one or more feet configured to be positioned in the anterior chamber, the one or more feet defining a convex curvature at a seating edge thereof, the seating edge being co-planar with a plane of the body; and
   c) a neck extending between the body and the feet and configured to be positioned in an opening in the sclera between the scleral recess and the anterior chamber, wherein the implant is configured to permit ocular fluid to drain out of the anterior chamber.

5. The implant of claim 4, wherein the body has one or more outer portions positionable in one or more undercuts extending outward from a recess in the sclera.

6. The implant of claim 4, wherein the body has one or more suture holes defined therein for receiving sutures.

7. The implant of claim 4, wherein the curvature at the seating edge is approximately the same as a curvature of the anterior chamber at the sclera.

8. The implant of claim 4, wherein the feet have outer portions that extend beyond a width of the body to stabilize the ophthalmic implant in the eye.

9. The implant of claim 4, wherein the neck has a length about one-fifth of a length of the body.

10. The implant of claim 4, wherein the neck has an approximate length of 0.8 mm.

11. The implant of claim 4, wherein the implant has one or more drainage passageways defined therein for the ocular fluid to flow through.

12. An ophthalmic implant for lowering the intraocular pressure of an eye having a selera and an anterior chamber, the implant comprising:
   a) a body configured to be positioned in a recess in the sclera;
   b) one or more feet extending directly or indirectly from the body and configured to be positioned in the anterior chamber, wherein the feet and the body combine to define opposing leading and trailing ends of the implant; and
   c) one or more drainage passageways defined in the implant for ocular fluid to flow through out of the anterior chamber, at least one of the passageways extending continuously from the leading end to the trailing end.

13. The implant of claim 12, wherein the drainage passageways include lateral drainage passageways for the ocular fluid to flow across the implant to disperse the ocular fluid into the sclera.

14. The implant of claim 12, wherein the drainage passageways include longitudinal drainage passageways for the ocular fluid to flow out of the anterior chamber and along the implant, and lateral drainage passageways for the ocular fluid to flow across the implant to disperse the ocular fluid into the sclera.

15. The implant of claim 12, wherein the drainage passageways comprise channels defined in one or more surfaces of the implant.

16. The implant of claim 12, wherein the drainage passageways comprise interior passageways defined in the implant.

17. The implant of claim 16, wherein the implant comprises two or more layers and the interior passageways comprise channels defined in one or more surfaces of the implant layers.

18. The implant of claim 16, wherein the implant comprises three or more layers and the interior passageways comprise voids defined in one or more inner layers of the implant.

19. The implant of claim 12, wherein the feet have a curvature that is approximately the same as a curvature of the anterior chamber at the sclera.

20. The implant of claim 12, wherein the feet have outer portions that extend beyond a width of the body to stabilize the ophthalmic implant in the eye.

* * * * *